(12) United States Patent
Barnes et al.

(10) Patent No.: US 10,929,972 B2
(45) Date of Patent: Feb. 23, 2021

(54) DEVICES, SYSTEMS AND METHODS FOR AUTOMATED QUANTITATIVE SCORING OF DIGITIZED TISSUE IMAGES

(71) Applicant: Ventana Medical Systems, Inc., Tucson, AZ (US)

(72) Inventors: Michael Barnes, Oro Valley, AZ (US); Joerg Bredno, San Francisco, CA (US); Christophe Chefd'hotel, San Jose, CA (US); Srinivas Chukka, San Jose, CA (US); Kien Nguyen, Ho Chi Minh (VN); Anindya Sarkar, Milpitas, CA (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 299 days.

(21) Appl. No.: 15/997,560

(22) Filed: Jun. 4, 2018

(65) Prior Publication Data
US 2018/0286043 A1    Oct. 4, 2018

Related U.S. Application Data

(63) Continuation of application No. PCT/EP2016/079655, filed on Dec. 2, 2016.
(Continued)

(51) Int. Cl.
*G06T 7/00* (2017.01)
*G06T 7/90* (2017.01)
(Continued)

(52) U.S. Cl.
CPC ....... *G06T 7/0012* (2013.01); *G01N 33/4833* (2013.01); *G06K 9/00127* (2013.01);
(Continued)

(58) Field of Classification Search
CPC . G06T 7/0012; G06T 7/11; G06T 7/90; G06T 2207/30024; G06T 2207/10056;
(Continued)

(56) References Cited

U.S. PATENT DOCUMENTS

2014/0185891 A1*  7/2014  Schoenmeyer ....... G06T 11/206
                                                                     382/128

FOREIGN PATENT DOCUMENTS

WO          2015124777  A1      8/2015
WO    WO-2015124777  A1 *   8/2015  ........... G06K 9/0014
(Continued)

OTHER PUBLICATIONS

Belien et al., Fully automated microvessel counting and hot spot selection by image processing of whole tumour sections in invasive breast cancer, Journal of Clinical Pathology, 1999, pp. 184-192, 52.
(Continued)

*Primary Examiner* — Amandeep Saini
(74) *Attorney, Agent, or Firm* — Kilpatrick Townsend and Stockton LLP

(57) ABSTRACT

Methods and systems for generating a heat map that reduces bias in selecting FOVs are disclosed. Some disclosed methods include annotating a primary stained image, registering the annotation to a secondary serial specific stained image, using an image analysis algorithm to compute a scoring criteria specific to the tissue and assay type for tiled regions in the image, using a sliding window in the annotated tumor region to compute values for each pixel in a heat map which correlate to the specific scoring criteria, displaying the heat map at low resolution, ranking and selecting hot spots, selecting FOVs from the hot spot regions which results in displaying the slide-level score for the FOVs. The systems comprise, among other things, software configured to perform the referenced method.

18 Claims, 11 Drawing Sheets

Related U.S. Application Data

(60) Provisional application No. 62/263,229, filed on Dec. 4, 2015.

(51) Int. Cl.
*G06K 9/00* (2006.01)
*G01N 33/483* (2006.01)
*G06T 7/11* (2017.01)

(52) U.S. Cl.
CPC .............. *G06T 7/11* (2017.01); *G06T 7/90* (2017.01); *G06K 2209/05* (2013.01); *G06T 2200/24* (2013.01); *G06T 2207/10036* (2013.01); *G06T 2207/10056* (2013.01); *G06T 2207/10064* (2013.01); *G06T 2207/20021* (2013.01); *G06T 2207/20104* (2013.01); *G06T 2207/20221* (2013.01); *G06T 2207/30024* (2013.01); *G06T 2207/30096* (2013.01)

(58) Field of Classification Search
CPC . G06T 2207/10036; G06T 2207/20021; G06T 2207/20104; G06T 2207/20221; G06T 2200/24; G06T 2207/10064; G06T 2207/30096; G06K 9/00127; G06K 2209/05; G01N 33/4833
USPC ........................................................ 382/128
See application file for complete search history.

(56) References Cited

FOREIGN PATENT DOCUMENTS

WO           2015181371 A1     12/2015
WO      WO-2015181371 A1 * 12/2015 ............. G06T 5/002

OTHER PUBLICATIONS

Brey et al., Automated Selection of DAB-labeled Tissue for Immunohistochemical Quantification, The Journal of Histochemistry & Cytochemistry, 2003, pp. 575-584, 51 (5).

Elie et al., A Simple Way of Quantifying Immunostained Cell Nuclei on the Whole Histologic Section, Cyometry Part A, 2003, pp. 37-45, 56A.

International Search Report and Written Opinion dated Mar. 23, 2017 in connection with PCT/EP2016/079655 filed Dec. 2, 2016 (32179 WO), pp. 1-14.

Molin, Jesper, et al., Feature-enhancing zoom to facilitate Ki-67 hot spot detection, Progress in Biomedical Optics and Imaging SPIE, (2014), 90410W-90410W, 9041.

Niazi et al., Hot spot detection for breast cancer in Ki-67 stained slides: image dependent filtering approach, Proceedings of SPIE, Medical Imaging 2014: Digital Pathology, 904106, 2014, pp. 1-9, 9041.

* cited by examiner

DEVICES, SYSTEMS AND METHODS FOR AUTOMATED QUANTITATIVE SCORING OF DIGITIZED TISSUE IMAGES

RELATED APPLICATIONS

This patent application is a continuation of International Patent Application No. PCT/EP2016/079655 filed Dec. 2, 2016, which claims priority to and the benefit of U.S. Provisional Patent Application No. 62/263,229, filed Dec. 4, 2015. Each of the above patent applications is incorporated herein by reference as if set forth in its entirety.

TECHNICAL FIELD

This specification relates to devices, systems, and methods for analysis of digitized images of tissue samples. For example, the specification describes methods for selecting regions of interest within a single or across multiple serial digitized slides of a tissue sample for automated or manual interpretation and scoring.

BACKGROUND

Digital Pathology refers to the management and interpretation of pathology information in a digital environment. Scanning devices are used to image slides of tissue sections, which may be stained, such that digital slides, e.g., whole slide images are generated. Digital Pathology software enables digital slides to be stored in a computer memory device, viewed on a computer monitor, and analyzed for pathology information.

Clinical diagnosis of cancer tissue may include a quantitative analysis of one or more types of biomarkers present within a tumor region. Generally, selection of "hot spot" regions—representative regions in the tissue slide of the biomarker overexpression—is done manually by a pathologist reviewing a digitized whole slide image of the slide stained for the specific biomarker on a computer screen. The selected hot spot regions may be analyzed either manually or using an image analysis algorithm used to detect the tumor cells and to quantify the specific biomarker expression and classify them as being marker positive or marker negative. Manual selection of hot spots introduces variability as different pathologists may select different regions as hot spots, thus potentially inducing variability in the clinical diagnostic score.

More specifically, in digital pathology, slide interpretation and quantitative scoring is manually or algorithmically done on a digitized immunohistochemical (IHC) tissue whole slide for prognostic and/or predictive diagnosis. In a first step for either a manual or algorithmic process, a pathologist visually reviews a digitized hematoxylin and eosin (H&E) whole slide image to identify the tumor region. In a subsequent step, in a manual process, the pathologist visually reviews the digitized whole slide on a whole slide viewer on a display monitor. Visually navigating the slide panning across the whole slide and switching between different magnifications, the pathologist picks representative sub regions in the whole slide image to score. Based on the tissue objects of interest (nuclei, membrane, glands etc.) and scoring protocol specific to the particular tissue indication and assay (be it a single-stained and multiple marker stained IHC assay), the appropriate score is estimated from these selected fields.

As an example, for clinical diagnosis of a breast cancer tissue from a patient, it is a common practice to stain tissue slides from adjacent serial sections in a tissue block with H&E, and four IHC markers (ER, PR, Ki67 and HER2). The H&E slide is used to identify the tumor region and to grade and stage the cancerous tissue. And in each of the IHC marker slides, i.e. ER, PR, Ki67 and HER2, the pathologist selects sub-images ("hot spots", fields of view ("FOVs")) within tumor regions to score. Based on the positively stained and negatively stained tumor nuclei for the marker, the specific signal is identified and enumerated. The enumeration may be used to compute metrics to quantify marker expression in terms of percent positivity, binned clinical score or H-score.

In an algorithmic analysis workflow, using a similar process like above, the pathologist visually reviews the slide, selects and annotates image sub regions ("hot spots") to be used for slide interpretation on the whole slide using a whole slide viewer. The image analysis algorithm takes as input the pathologist annotations and the scanned whole slide image. Then the image analysis algorithm, specific to the marker and tissue type, is used to analyze the selected sub-images, automatically detecting and classifying the objects of interest (like tumor nuclei, with nuclear, cytoplasmic or membranous staining for the specific marker) and counting and scoring the detections according to the scoring protocol specific to the tissue type and assay.

It can be observed that in both the workflows, the selection of sub-images to score is both a vital step and a manual process, which impacts the clinical score and end diagnostic output. That is, scanned slide tissue is viewed by independent readers, and FOVs are manually marked based on the readers' personal preferences. After selecting the FOVs, either the computer produces counts of immune cells in each Field of View ("FOV") via an automatic algorithm or a pathologist/reader manually counts the immune cells within the selected FOVs. Because manual selection of the FOVs is highly subjective and biased to the readers, as different readers may select different FOVs to count, scoring reproducibility is a challenge.

Accordingly, the present disclosure aims to remedy the deficiencies attendant the prior art by providing a novel and improved system and/or method that reduces or eliminates subjectivity and bias in identifying FOVs. That the methods of the present disclosure are superior to those allegedly disclosed in the prior art will become readily apparent from the discussion below.

Automated methods of FOV selection are allegedly disclosed, such as:

Brey, Eric M., et al. "Automated selection of DAB-labeled tissue for immunohistochemical quantification." Journal of Histochemistry & Cytochemistry 51.5 (2003): 575-584;

Belien, J. A., et al. "Fully automated microvessel counting and hot spot selection by image processing of whole tumour sections in invasive breast cancer." Journal of clinical pathology 52.3 (1999): 184-192;

Elie, Nicolas, et al. "A simple way of quantifying immunostained cell nuclei on the whole histologic section." Cytometry Part A 56.1 (2003): 37-45;

Muhammad Khalid Khan Niazi et al., Hot spot detection for breast cancer in Ki-67 stained slides: image dependent filtering approach, SPIE Medical Imaging, 2014.

Jesper Molin et al, Feature-enhancing zoom to facilitate Ki-67 hot spot detection, SPIE Medical Imaging, 2014.

However, the methods disclosed in the prior art noted above are based on local averaging or image filtering of the marker stain component image (example: DAB stain component image derived from the IHC image using color deconvolution algorithm) from the IHC whole slide at a lower resolution, and picking the regions where the biomarker is overexpressed as "hot spots." Such an approach has a number of limitations, including, for example, the following:

1) Because selection is based on local averaging at low magnification, it does not adequately capture weakly positive or small regions with invasive tumors where the tumor cells are dispersed amongst a bed of non-tumorous cells, which may in fact be hot spots with aggressive tumor.
2) The prior art approach assumes that the positive staining is specific to a tumor alone and all regions with any positive staining can be considered as hot spots. In such a scenario, the non-specific regions or any image regions with staining artifacts may be ranked above and picked as the "hot spots" over the real tumorous hot spots.
3) The conventional approach implicitly assumes the high expression of positive staining as a surrogate for the tumor hot spots, which is not always true. In picking tumor hot spots an expert such as pathologist takes into consideration the tumors and the aggressive nature of the underlying epithelial cells. Consequently, this approach is different from the criteria used by the pathologist in annotating the tumor hot spots.

Disclosed herein is a semi-automated workflow to assist in the selection of sub-image regions to score. The method analyzes inter alia the whole slide and identifies and ranks potential tumor "hot spots" in the whole slide based on image analysis methods adopting similar tumor interpretation guidelines used by pathologists. In illustrative embodiments, the method includes presenting to the pathologist a slide representation which highlights the FOVs with tumor hot spots to pick from them.

While certain novel features are shown and described below, some or all of which may be pointed out in the claims, the devices, systems and methods of the present disclosure are not intended to be limited to the details specified, since a person of ordinary skill in the relevant art will understand that various omissions, modifications, substitutions and changes in the forms and details of the illustrated embodiments and in their operation may be made without departing in any way from the spirit of the disclosure. No feature described herein is critical or essential unless it is expressly stated as being "critical" or "essential."

SUMMARY

The methods and systems of the present disclosure provide an automated or semi-automated (hereinafter "semi-automated") workflow to assist in consistent selection of sub-regions of digitized images to score. In some embodiments, the methods and systems result in analysis of the whole slide, and identification and ranking of potential hot spots (regions which have a high density of marked objects) facilitating and improving the accuracy of Fields of View selection.

In some embodiments, the method involves generating a heat map representative of a specific scoring criteria, which heat map reduces bias in identifying and selecting FOVs. In some embodiments, generating the heat map involves generating a low-resolution heat map by computing a scoring criteria specific to the tumor and staining type at scanned resolution and correlating pixel values in the heat map to the scoring criteria. In some other embodiments, generating the heat map involves annotating a tumor image on a digitized primary staining slide image, registering the annotations from the digitized primary staining slide to a digitized specific staining slide image, and generating a low-resolution heat map by computing a scoring criteria specific to the tumor and staining type at scanned resolution and correlating pixel values in the heat map to the scoring criteria. In further embodiments, computing the scoring criteria involves gridding the annotated tumor region in the digitized specific staining slide image into tiles of a predetermined size and computing the scoring criteria for each tile at scanned resolution. In other further embodiments, correlating pixel values I the heat map to scoring criteria involves computing an average value for the scoring criteria in a windowed region of predetermined size in the annotated tumor region in the digitized specific staining slide image which average value correlates to a pixel value, and sliding the windowed region across the annotated tumor region to iteratively compute pixel values and thereafter generate an interpolated image of the low resolution heat map from the computed pixel grid values of the score values. In some embodiments, the methods further include using an algorithm to rank, select and highlight hot spot regions having a high density of specific staining. In some such embodiments, ranking involves selecting local maxima within a predetermined neighborhood of values in the heat map and sorting them in order.

In some embodiments the systems include a plurality of processing modules or logical operations that are executed by a processor, wherein the modules includes a heat map generation module and may also include one or more of an annotation module, an image registration module and an FOV selection module. In further embodiments, the systems also include one or more of a source for generating a digitized image of a staining slide, a memory in communication with the source, a processor and a computer interface. In some embodiments, the modules are configured to execute a computer-implemented method for reducing bias in identifying and selecting FOVs by loading a list of image files for a case, the image files including at least a digitized primary staining slide image and a digitized specific staining slide image, enabling a user to annotate or to include annotated images of a tumor area within the digitized primary staining slide image, registering annotations from the digitized primary staining slide image to the digitized specific staining slide image, computing a specific scoring criteria at scanned resolution across the annotated region within the digitized specific staining slide, generating a low-resolution heat map image of the digitized specific staining slide image wherein a pixel value in the heat map corresponds to an average value of the specific staining slide, enabling a user to zoom in and out of the heat map to view one or more regions, and enabling the user to select a FOV from the heat map, resulting in displaying the computed scoring criteria at scanned resolution for the FOV.

While the disclosure provides certain specific embodiments, the disclosure is not limited to those embodiments. A person of ordinary skill will appreciate from the description herein that modifications can be made to the described embodiments and therefore that the specification is broader in scope than the described embodiments. All examples are therefore non-limiting.

DETAILED DESCRIPTION

Figure 1:
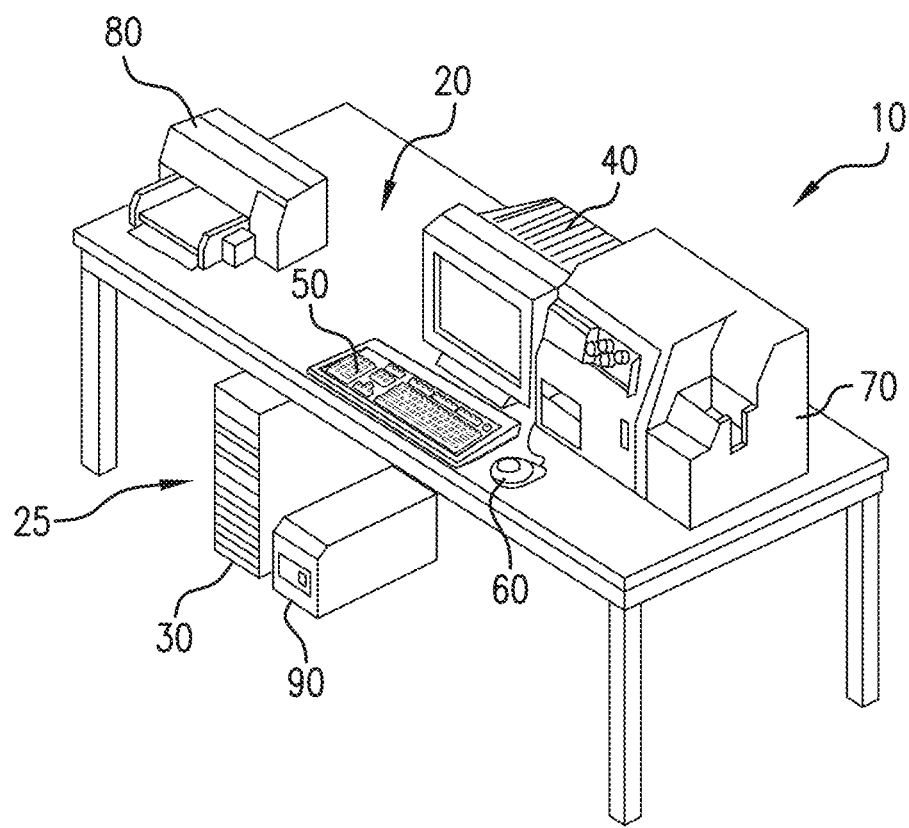
FIG. 1 is a perspective, pictorial representation of an embodiment of a medical imaging workstation system in which the devices, systems and methods according to the disclosure may be implemented.

Detailed descriptions of one or more embodiments are provided herein. It is to be understood, however, that the devices, systems and methods according to this disclosure may be embodied in various forms. Therefore, specific details disclosed herein are not to be interpreted as limiting, but rather as a representative basis for the claims and for teaching one skilled in the art to employ the present devices, systems and methods in any appropriate manner.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" is meant to account for variations due to experimental error. All measurements or numbers are implicitly understood to be modified by the word about, even if the measurement or number is not explicitly modified by the word about.

The terms "comprising" and "including" and "having" and "involving" and the like are used interchangeably and have the same meaning. Similarly, "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Where the terms "a" or "an" are used, "one or more" is understood unless explicitly stated otherwise or such interpretation is nonsensical in context.

A "heat map" is a low-resolution image of the whole slide (or desired portion thereof), wherein a pixel value in the heat map corresponds to the value computed according to a specific scoring criteria adopted to evaluate the marker slide. Visually, a heat map is a high-level overview visual representation of the scoring metric of interest. For example, for a Ki67 IHC stained slide, a pixel value corresponds to percent positivity in a pre-defined sub-region of the tumor region, and the heat map provides a high-level overview of percent positivity across the tumor region in the whole slide (or desired portion thereof).

A "hot spot" is a region in the heat map, which is locally dominant. A pathologist may consider one or more hot spots to be important and select the Fields of View from the hot spots presented for visual review to compute the slide level score.

The present disclosure relates to Digital Pathology and provides methods and systems for identifying hot spot regions in biological tissue samples, which are compatible with automated (e.g. computerized) digital tissue image analysis. The methods include for example a semi-automated workflow and algorithm (i.e. a computer-implemented method) for generating a heat map facilitating accurate identification of hot spot regions and potential FOVs for slide level scoring. The methods can be applied to single or multiple sets of slides, such as any single or multiple set of IHC assay stained slides (e.g., ER, PR, Ki67, HER2, Dual ISH, CD3, CD8, c-MET, PD-L1) of any biological specimen tissue and of multiple disease types (e.g., breast, prostrate, colon, brain). The systems include computerized systems including non-dedicated computerized systems.

In some embodiments, the methods and systems are implemented on a stand-alone workstation (which may include a modem for access to the interna). In yet other embodiments, the devices, systems and methods may be implemented over a computer network. Whether implemented on a stand-alone workstation or over a network, the systems according to the present disclosure may include at least some of the following hardware components: a computer comprising an output device for displaying images and/or results such as a monitor and one or more input devices such as a keyboard and mouse or trackball for interacting with software programs, and a processor for executing the software programs. The systems may also include a storage device for storing digital image files. The systems may also include a scanner for producing digital image files from slides of stained tissue specimens.

Whether implemented on a stand-alone workstation or over a network, the systems may include one or more of the following software components: a heat map generation module, and an image display module. The systems may also optionally include one or more of the following software components: an annotation module, an image registration module, and/or an FOV selection module. The modules may be separate modules or one or more modules may be combined as a single module. For example, the functions of the annotation module may be combined with that of the FOV selection module. Furthermore, while the modules are described as software modules, it is appreciated by a person skilled in the art that in various embodiments, each module can be implemented as any combination of software, firmware, or hardware (e.g., circuitry).

Figure 5:
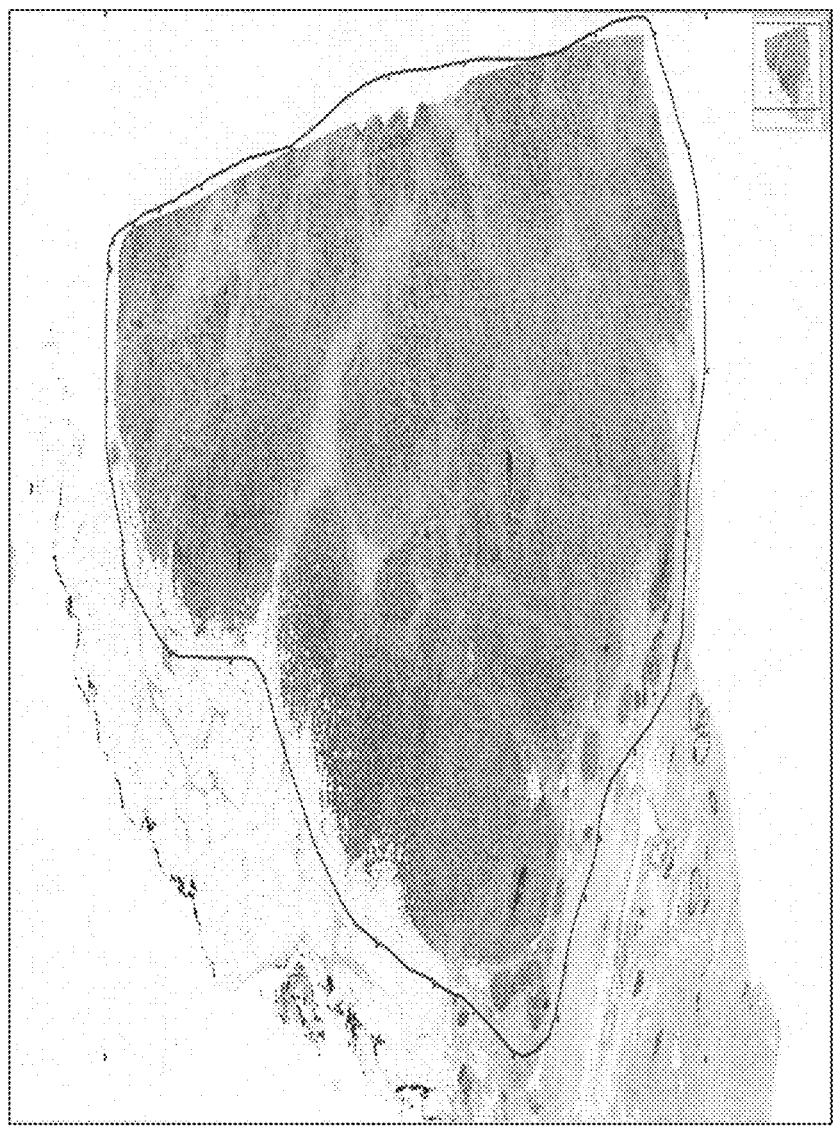
FIG. 5 is a screen shot of an annotation module GUI after a primary digital staining slide has been selected and annotated.
Figure 6A:
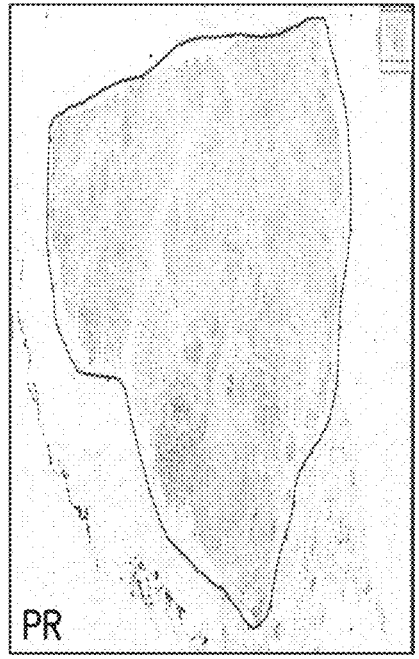
FIGS. 6A-6D are screen shots of an image registration module GUI, after the annotation from the primary staining slide has been transferred to digitized specific staining slide images.
Figure 6B:
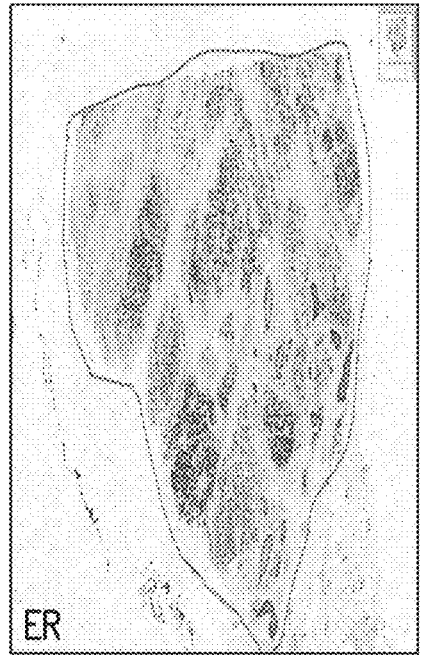
Figure 6C:
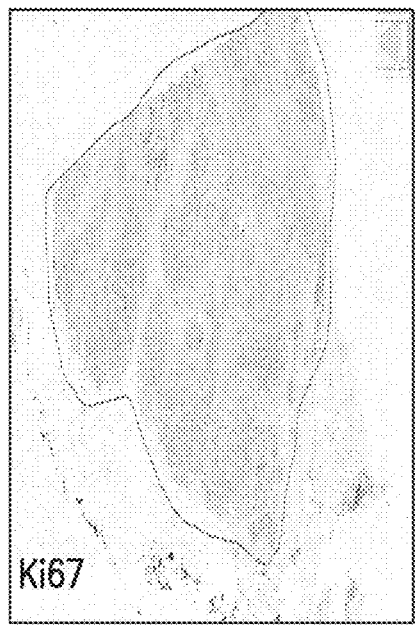
Figure 6D:
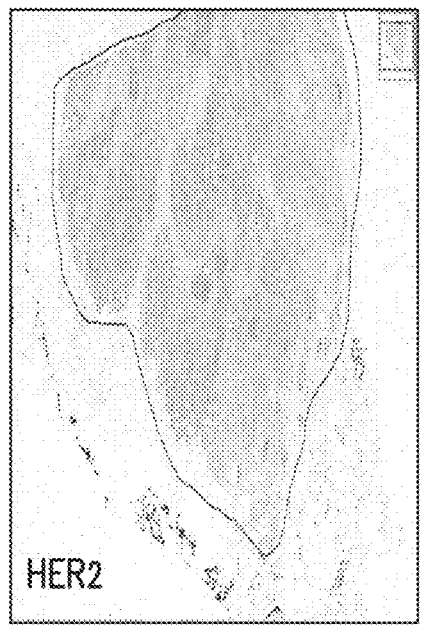

The annotation module, when executed by the processor, results in identification of regions of interest for analysis, and may also result in identification of regions to exclude from analysis. For example a slide, such as an H&E stained slide, is digitized and annotated to identify the entire tumor region as shown in FIG. 5. Optionally, the slide may also be annotated to exclude regions from analysis such as normal tissue regions and/or necrotic regions. The annotations may be automatically generated by an image analysis algorithm and/or they may be manually identified by a user.

The image registration module, when executed by the processor, results in the transfer of annotations from a first image (such as an H&E stained slide image) to one or more second images (such as IHC stained serial slides). In FIG. 6, the annotations from the H&E stained primary slide in FIG. 5 have been transferred to a PR-IHC stained serial secondary slide (6a), an ER-IHC stained serial secondary side (6b), a Ki67-IHC stained serial secondary slide (6c), and an HER2 stained serial secondary slide.

The heat map generation module, when executed by the processor, computes a scoring criteria relevant to the specific tissue and assay under investigation at, for example, the scanned resolution, and generates a visual display reflective of the scoring criteria and therefore potential hot spots (regions containing a high density of marked (e.g., stained) cells) on the digitized image at a lower resolution. The "lower" resolution is chosen to enhance a user's ability to easily identify hot spots and select FOVs for evaluating the biological specimen. In some embodiments multiple scoring criteria are computed and a heat map is generated for each of the computed multiple scoring criteria. For example, a user may instruct the heat map generation module to compute an H-score, percent positivity and an All Red score resulting in generating multiple heat maps, each corresponding to one of the scoring criterion.

As an example, the heat map generation module may first involve an image analysis module followed by a low-resolution heat map generation module.

Figure 7:
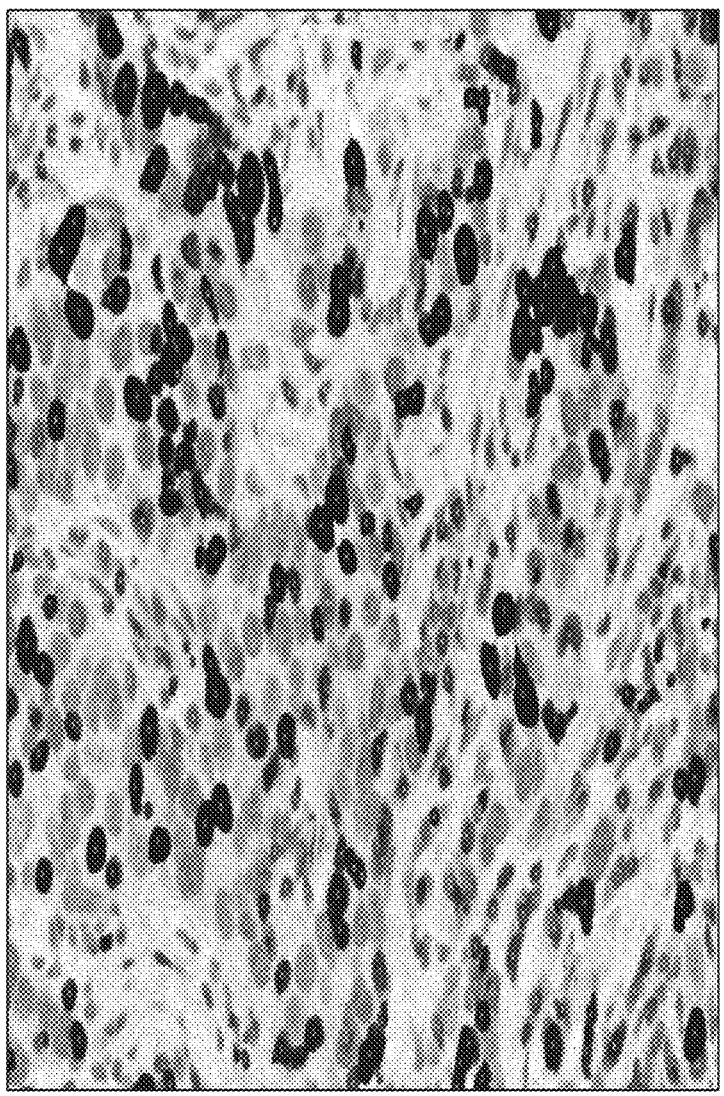
FIG. 7 is a screen shot displaying the image analysis results for a single Ki67 IHC image tile, which is produced during the heat map generation process. Green (visible as light grey spots in the center of the black shapes in FIG. 7) indicates negative tumor nuclei and red (visible as dark grey spots in the center of the black shapes in FIG. 7) indicates positive tumor nuclei.
Figure 8:
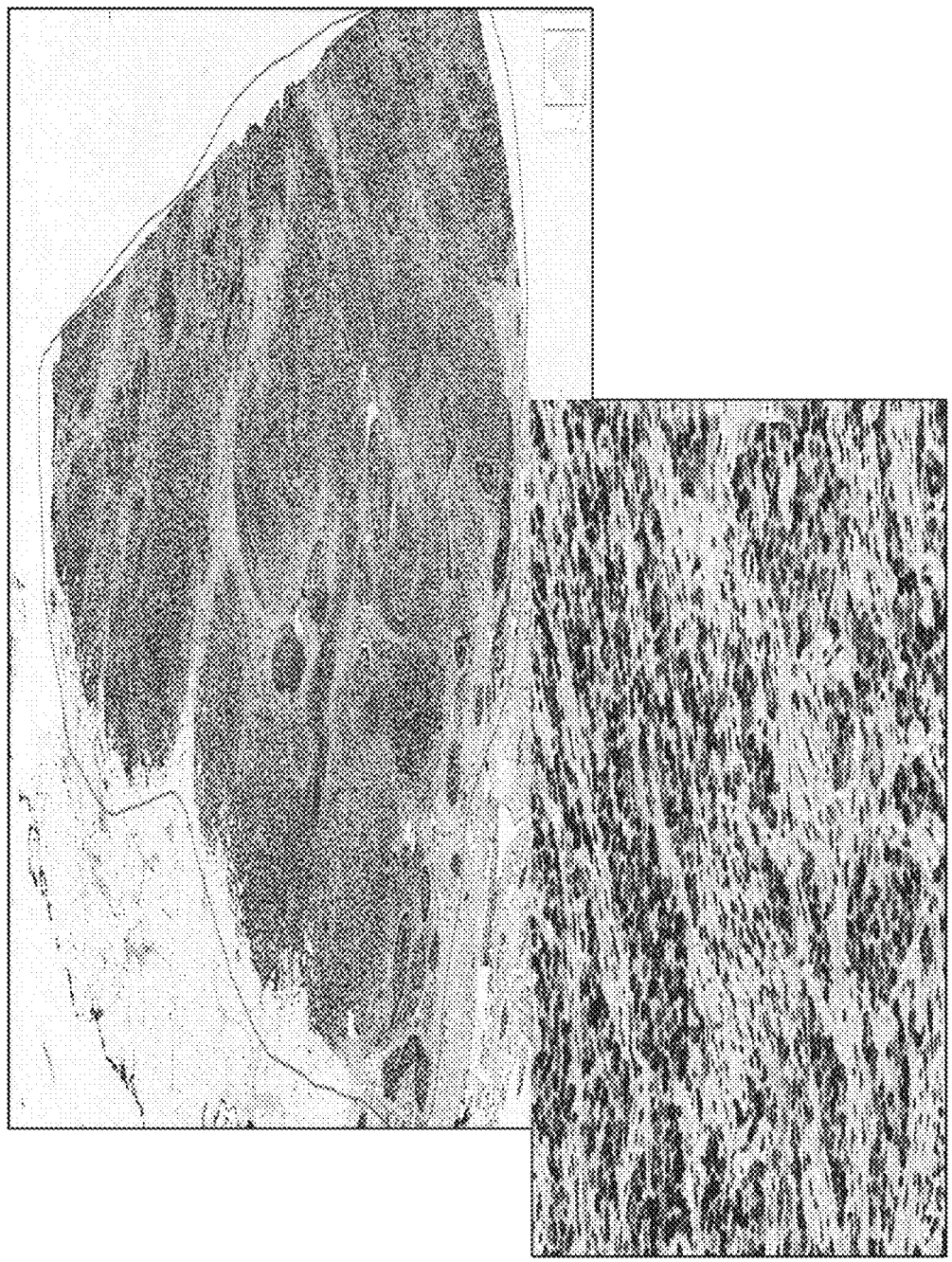
FIG. 8 is a screen shot depicting the whole tumor slide analysis result for the Ki67 IHC slide of FIG. 7, with a blow up of a result from a small region within the whole slide.

The image analysis module, when executed by the processor, results in computing a scoring criteria relevant to the specific tissue under investigation and the specific assay across the whole serial secondary stained slide or slides. FIGS. 7 and 8 illustrate the output of the image analysis module for the Ki67 IHC stained serial section slide, which detect, counts and classifies positive and negative tumor nuclei. FIG. 8 illustrates a display of the results over the whole slide image, including a blow up result from a small region of the image. FIG. 7 illustrates the results for a specific "tile" region of the whole slide of FIG. 8, and in which green indicates negative tumor nuclei (visible as light grey spots in the center of the black shapes in FIG. 7) and red indicates positive tumor nuclei (visible as dark grey spots in the center of the black shapes in FIG. 7). Because the whole tumor region can be quite large, the tumor is gridded into tiles and the image analysis is done on the individual tiles for computational efficiency considerations.

The low-resolution heat map generation module, when executed by the processor, computes a pixel value corresponding to the average value of the scoring metric of interest (image analysis results) for an entire sliding window resulting in a visual display useful in identifying potential "hot spots" (regions containing a high density of marked (e.g., stained) cells) on the digitized image. To compute the heat map at all the pixels, the score values are computed on a pixel grid with a sliding and overlapping window. The sliding window and overlapping size are user chosen parameters. The parameters are chosen such that the area is small enough to compute a locally meaningful score and large enough to have enough tumor nuclei samples in the window to obtain a statistically meaningful estimate of the score. In some embodiments, the sliding window dimensions may correspond to a typical-sized image region that a pathologist uses to estimate the average scoring metric values for the region. The overlapping window size is chosen to be able to compute the heat map values on a regularly sampled grid on the image plane and accurately interpolate a smooth varying heatmap for visual display.

Figure 9:
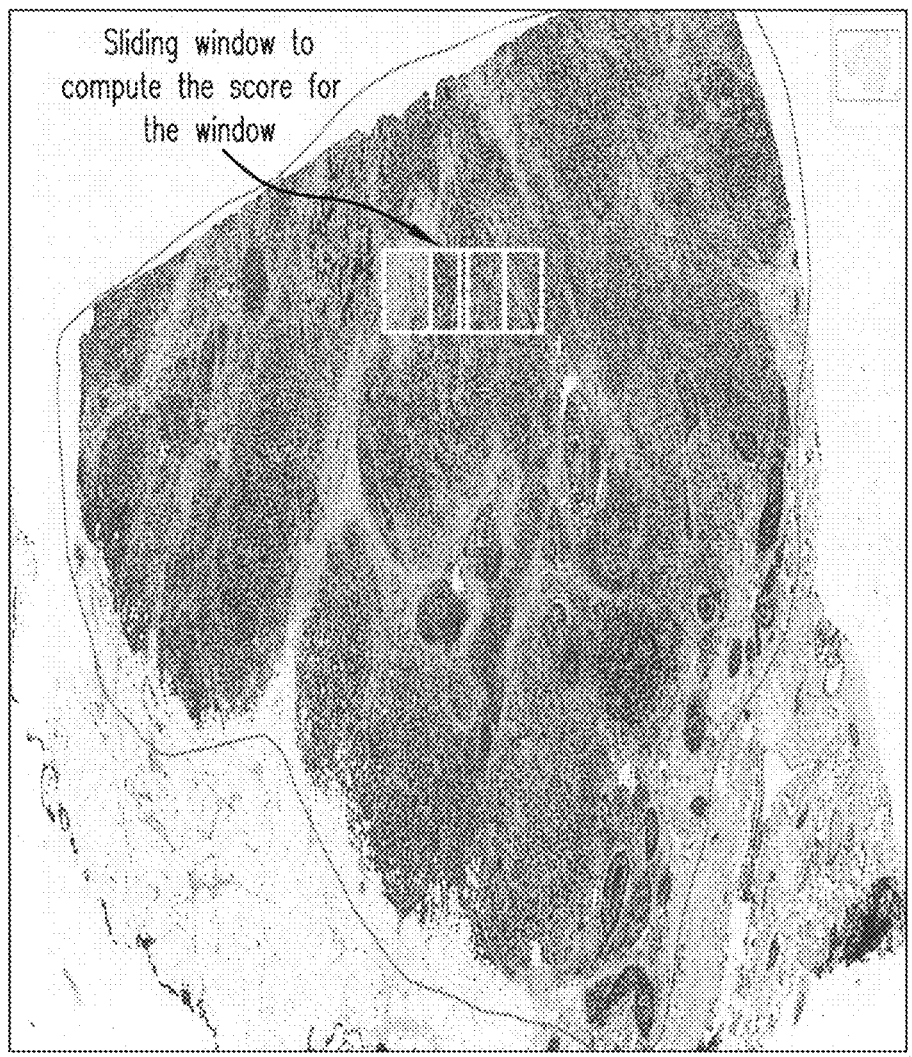
FIG. 9 is a screen shot illustrating an embodiment of a method for generating a heat map from the image analysis results of FIG. 8, specifically illustrating the sliding window use to compute the value for the corresponding pixel in the heat map.

For example, FIG. 9 illustrates a sliding window used to compute the value for a pixel in the heat map. Specifically, a pixel value corresponds to the percent positivity for the window in the Ki67 IHC slide, and is computed as the percentage of Ki67 stained positive nuclei in the total tumor nuclei within the windowed region. And, in the illustrated image, the window to compute the percentage positivity score was chosen to be a 1 mm squared region, which corresponds to a typical field of view that is visible to the pathologist thru the eyepieces under a microscope at a typical total magnification with a 20× objective lens, and the overlapping size was chosen to be 0.75 mm. The chosen values correspond to computing the score for a pixel window of size 2000×2000 at the scanned 20× resolution (with a scanner pixel size=0.5 um), and with an overlapping slide window of 0.75 mm, the pixel values in heat map is computed at 0.25 mm pitch in either direction. More specifically, for a scanner pixel size=0.5 um at 20× magnification, 1 mm physical length on the slide corresponds to 2000 pixels. Pixels=Pixel Size (pixels/mm)*Field of view (in mm) Thus a 1 mm×1 mm field of view area corresponds to a 2000×2000 pixel sized area of the scanned image.

Figure 10:
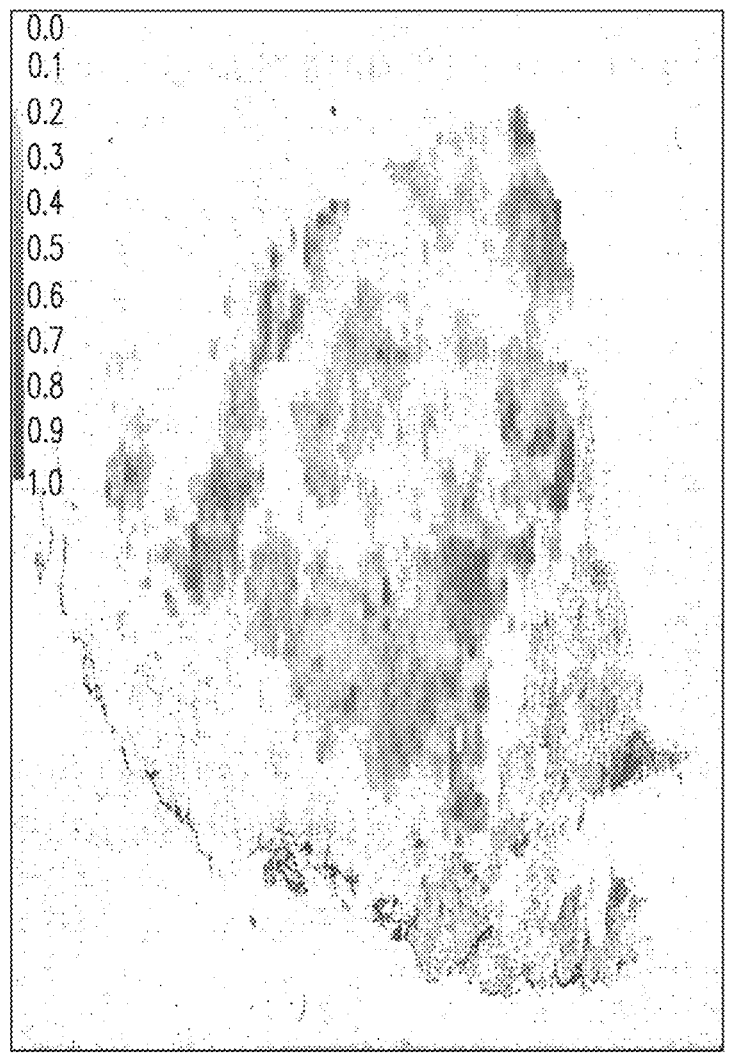
FIG. 10 is a screen shot of the heat map which is generated from the computations performed on the basis of Ki67 IHC slide image data as shown in FIGS. 8 and 9.

From the computed pixel grid values of the score values, an interpolated image of the heat map is generated for display. FIG. 10 illustrates the heat map showing percent positivity for the annotated tumor region of the Ki67 IHC stained slide from FIG. 6c resulting from the heat map pixel values computed in the sliding window illustrated in FIG. 9. The computed score values (percent positivity etc.) can be interpolated to such a finer grid as shown in FIG. 10 by employing standard image 5 interpolation methods, such as bilinear interpolation, bicubic interpolation or nearest neighbor interpolation algorithms. See also Digital Image Processing, Gonzalez and Woods, 3rd Edition. To interpolate 10 continuous scoring metrics such as percentage positivity and H-score, bilinear and bicubic interpolations methods are used. In a bilinear interpolation method, the value at the interpolated location is obtained as a weighted average of the four surrounding locations where the computed score values with the weights determined by the distance of the interpolated location to them. To interpolate the binned score metrics (such as the membranous binning scores such as 0+, 1+, 2+, 3+ used for HER2 slide scores), nearest neighbor interpolation schemes are adopted. In the nearest neighbor interpolation scheme, the value at the interpolated location is assigned the same value as that of the nearest location with 20 the computed score value (see, e.g., Gonzalez and Woods referenced above). Typically, the heat map thumbnail is interpolated to either 2× or 4× magnification to be displayed on the computer monitor for visualization of the heat map by the pathologist to easily identify the hot spots therein, which corresponds to a pixel size of around 16 um or 32 um. Thus, a computed heat map of M×N locations is 25 interpolated to a 16×M×16×N lattice grid, i.e., 16 points in between every two sample locations are interpolated.

Figure 11:
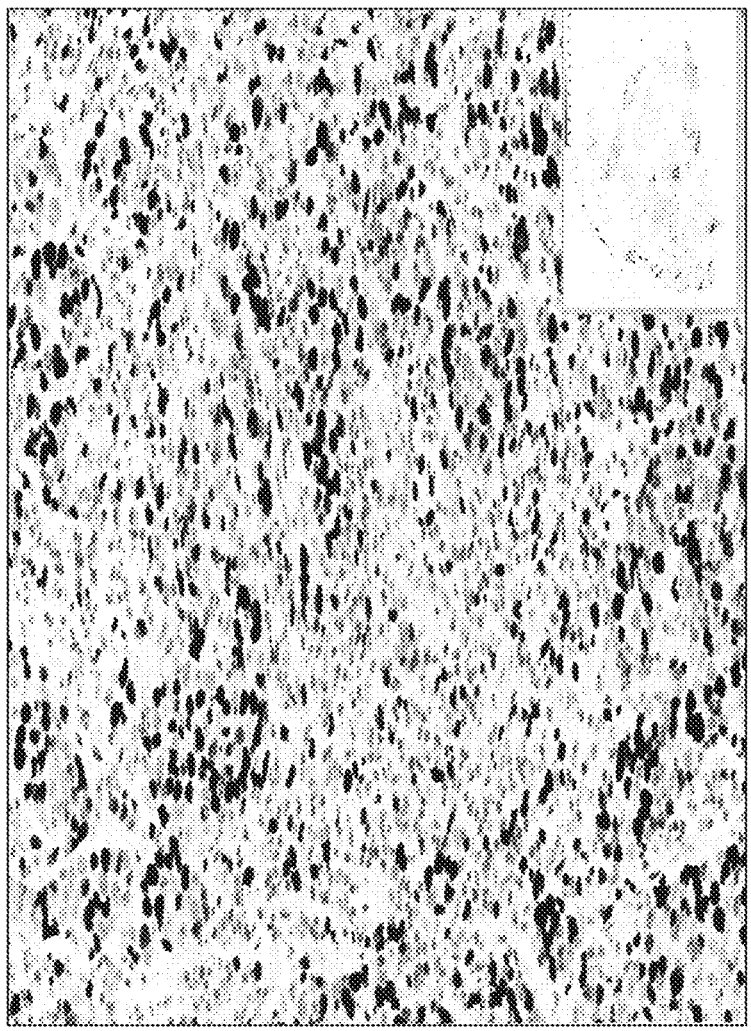
FIG. 11 is a screen shot, which illustrates a use of the heat map, shown in the highlighted window in the thumbnail. The main screen shows the high resolution image (the scanned resolution) of the highlighted window (FOV) in the thumbnail.

The FOV (Field of View) selection module, when executed by the processor, results in selection of a region of the image for further analysis and for example may result in providing a detailed image of the selected region and/or its related analyzed and scored image data such as IHC slide-level score that was previously computed by the image analysis module at scanned fine resolution. FIG. 11 illustrates the computed heat map in the thumbnail display window with an FOV selected, and illustrates the analyzed result for the FOV (portion of the whole slide) at the original scanned resolution in the main display.

The image display module, when executed by the processor, results in at least providing a digital image displaying slide images and/or results, for example slide images, which have been annotated such as to depict tumor regions or to depict potential hot spot regions. The image display module, when executed by the processor, may result in an interactive digital image, for example a heat map image in which a user may rank, select and/or visually highlight potential hot spots, and/or which may permit a user to select one or more FOVs (for example from the highlighted hot spots) resulting in providing a detailed image of the selected region and/or its related image data such as IHC slide-level score that was previously computed by the image analysis module.

In some embodiments, where multiple scoring criteria are used to evaluate a same tissue slide, the whole tissue slide image is scored with each of the scoring criteria and a heat map is computed and generated as described above for each of the scoring criteria. And as part of the FOV selection module, a menu option is provided for the user to choose and upload any of the computed heat maps for display in the thumbnail window and accordingly provide a detailed image, as described above, from the corresponding whole image result data.

Computer-implemented methods according to this disclosure comprise: a computer-implemented analysis process for identifying one or more hotspots in a digitized image of a biological slide (such as a slide of a tissue sample) that has been stained (for example, with flourophores, quantum dots reagents, tyramides, DAPI, etc.). In some embodiments, the tissue sample has been stained with only a single stain. In some embodiments, the tissue sample has been stained with more than one stain. Although specific examples herein refer to slides having only one stain, a person of skill can apply the teachings herein to multiplexed slides. For example, the multiplexed slide may undergo an unmixing process to simulate multiple single-stained slides and the process can be applied to each of the unmixed channels to compute hot spots and to follow up with any further marker co-expression analysis.

Referring back to the Figures, wherein like reference numerals refer to like parts throughout, FIG. 1 is a perspective, pictorial representation of an embodiment of a medical imaging workstation system 10 in which the devices, systems and methods according to this disclosure may be implemented. As shown, the medical imaging workstation system 10 includes a computer 20 having a housing for hardware components 30 such as a processor ("CPU") (not shown), a storage device (not shown), a graphics processor unit ("GPU") (not shown), and optionally a modem (not shown); a first output device, which in the illustrated example is a monitor 40; a first user input device, which in the illustrated example is a keyboard 50; and, a second user input device, which in the illustrated example is a pointing device for interacting with the display such as a track ball or mouse 60. As is known in the art, although the computer 20, hardware component 30, monitor 40, and user input devices 50, 60 are illustrated as separate components, they may be integrated in fewer parts such as they may all be integrated in the form of a laptop computer. The medical imaging workstation system 10 may also include additional peripherals such as a third input device, which in the illustrated example is a slide scanner 70, a second output device, which in the illustrated example is a printer 80, a back-up power supply 90, and external storage devices (not shown), among other devices which are known to be associated with computer-implemented medical imaging systems. In some embodiments, the medical imaging workstation system 10 may include more than one monitor 40 for ease of simultaneous viewing of multiple digital tissue images on multiple screens. As a person of skill appreciates, the specific components may change as technology changes. For example, a peripheral pointing device may not be necessary if the screen is responsive to a user's finger, or voice commands.

The medical imaging workstation system 10 also includes software components such as a hot spot identification program and an image display program. In some embodiments, the hot spot identification program comprises an annotation module, an image registration module, an image analysis module, and a heat map generation module. The software components may be one or more files, which are stored on the storage device (for example the software components may be stored on an internal hard drive) and/or the software components may be stored on a memory disc such as a DVD, CD or memory card, which can be accessed by the processor when the memory disc is inserted into the housing 30 through a memory-disc receiving port 25.

The CPU is operatively connected to the various peripherals and hardware components, including the storage device and the GPU. The storage device may temporarily or permanently store digital images, which may be imported into the system, for example by a scanning device. The digital images may include one or more digital images of adjacent tissue sections from a patient or from an archived tissue sample, wherein the images may be of a tissue section or group of adjacent serial sections stained to evaluate a problem of interest. For example, for clinical diagnosis of breast cancer tissue from a patient, tissue slides from adjacent serial sections in a tissue block may be stained with H&E and four IHC markers (ER, PR, Ki67, and HER2) respectively. The GPU processes instructions from the software modules. When executed, for example by the GPU, the image display program may provide a windowed graphical user interface ("GUI") on the monitor 40 with multiple windows such that a user may interact with the GUI to provide instructions resulting in a processor, such as for example the CPU, executing one or more aspects of the image analysis program, and/or may result in displaying one or more of the stored digital images on one or more of the monitors 40, either in their native (originally-scanned) format or as modified by the image analysis program.

Figure 3:
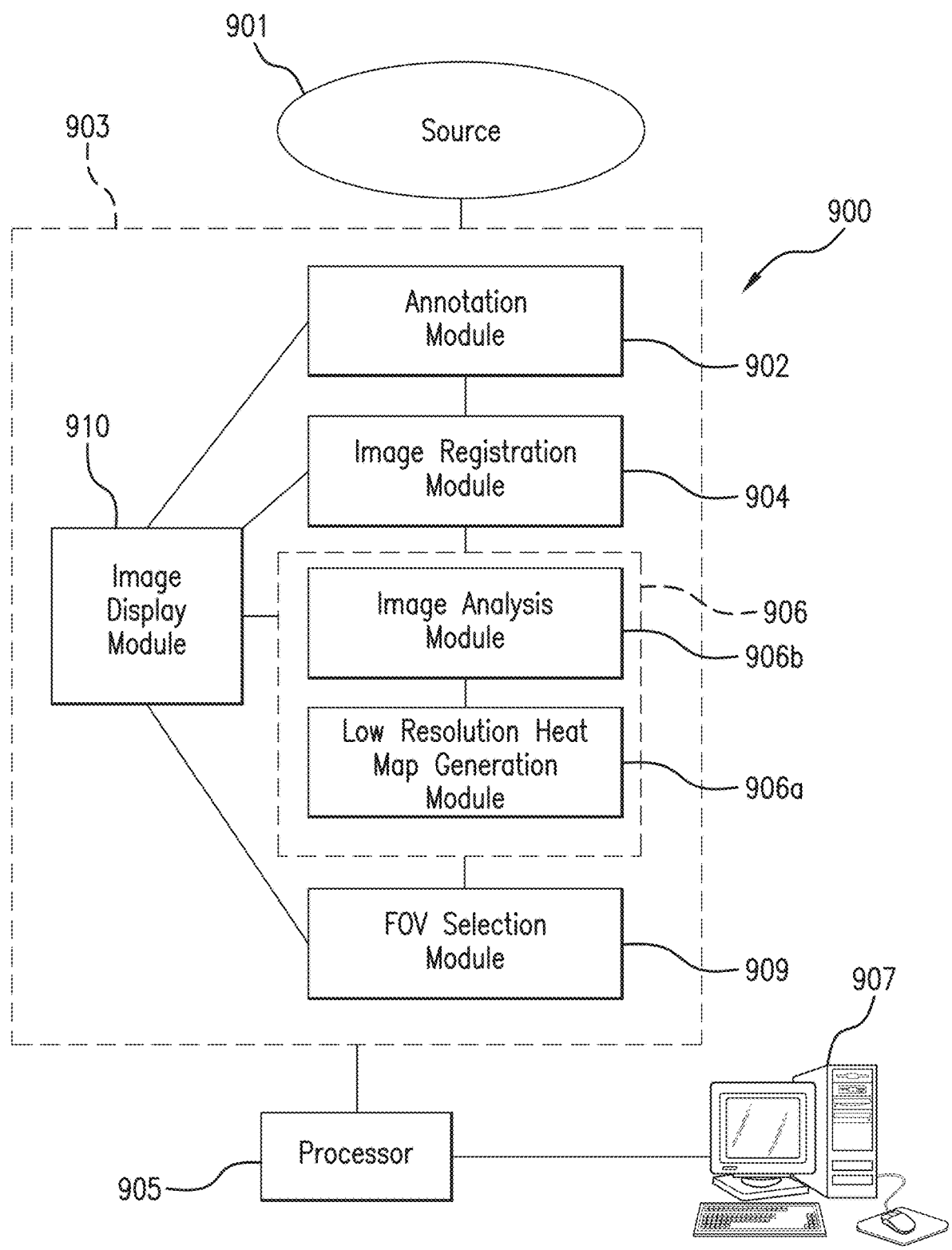
FIG. 3 illustrates a system according to at least one embodiment of the disclosure.

FIG. 3 illustrates a system 900, for example, an imaging system for image analysis in accordance with an exemplary embodiment of the present subject disclosure. System 900 comprises a source 901 for generating a multi-channel image or multi-channel image data (for example, an RGB image or RGB image data and/or a multispectral image or multispectral image data). For instance, source 901 may be or include a fluorescence microscope, camera, optical, scanner, CCD, or imaging system that generates a fluorescent image, or a bright-field microscope, camera, optical scanner, or imaging system generating an RGB image, multispectral image, and/or RGB or multispectral image data. Examples of imaging systems can be, for example, any fluorescent or a brightfield microscope with spectral filter wheel or a whole slide scanner. Source 901 is in communication with a memory 903, which includes a plurality of processing modules or logical operations that are executed by processor 905 coupled to computer interface 907. For instance, a sample, such as a biological specimen, may be mounted on a slide or other substrate or device for purposes of imaging by a microscope, camera, scanner, CCD, or other optical system 901 coupled to memory 903, with analysis of images of the specimen being performed by processor 905 executing one or more of the plurality of modules stored on memory 903 in accordance with the present disclosure. The analysis may be for purposes of identification and study of the specimen. For instance, a biological or pathological system may study the specimen for biological information, such as the presence of proteins, protein fragments or other markers indicative of cancer or other disease, or for other purposes such as genomic DNA detection, messenger RNA detection, protein detection, detection of viruses, detection of genes, or other.

The specimen, for example, a tissue specimen or cytology specimen may be stained by means of application of one or more different stains that may contain one or more different quantum dots, fluorophore(s), or other stains. For example, in a fluorescent slide, the different stains may correspond to different quantum dots and/or fluorophores. The fluorophores may comprise one or more nano-crystalline semiconductor fluorophores (e.g., quantum dots), each producing a peak luminescent response in a different range of wavelengths. Quantum dots are well known, and may be commercially available from Invitrogen Corp., Evident Technologies, and others. For example, the specimen may be treated with several different quantum dots, which respectively produce a peak luminescent response at 565, 585, 605, and 655 nm. One or more of the fluorophores applied to the specimen may be organic fluorophores 14 (e.g., DAPI, Texas Red), which are well known in the art, and are described in at least commonly-owned and assigned U.S. Pat. No. 8,290, 236, the contents of which are incorporated by reference herein in their entirety. Moreover, a typical specimen is processed utilizing a staining/assay platform, which may be automated, that applies a stain, for example, a stain containing quantum dots and/or organic fluorophores to the specimen. There are a variety of commercial products on the market suitable for use as the staining/assay platform.

After preliminary tissue processing and staining, one or more digital images of the specimen may be captured at source 901 via, for instance, a scanner, CCD array spectral camera, or other imaging system that is used for imaging a slide containing a sample of a material, and generate a digital image of the sample on the slide. The slide containing the sample is subjected to a light source for illuminating the specimen at wavelengths intended to produce a luminescent response from the stain applied to the specimen. In the case of quantum dots, the light source may be a broad spectrum light source. Alternatively, the light source may comprise a narrow band light source such as a laser. An RGB brightfield image may also be captured. The imaging system may include, for example, a digital camera, a microscope or other optical system having one or more objective lenses, and light sources, as well as a set of spectral filters. Other techniques for capturing images at different wavelengths may be used. Camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure. The image may be supplied to memory, or storage device 903, either via a wireless or wireline connection, for example, a cable connection between the source 901 and computer 907, via a computer network, or using any other medium that is commonly used to transfer digital information between computers. The image may also be supplied over the network to a network server or database for storage and later retrieval by computer 907. Besides processor 905 and memory 903, computer 907 also includes user input and output devices such as a keyboard, mouse, stylus, and a display/touchscreen. As will be explained in the following discussion, processor 905 executes modules stored on memory 903, performing analysis of the image, of the image or image data derived from such images, quantitative analysis, and display of quantitative/graphical results to a user operating computer 907.

Modules stored on memory 903 may include an annotation module 902, an image registration module 904, a heat map generation module 906 (which in some embodiments comprises an image analysis module 906b and a low-resolution heat map generation module 906a), an FOV selection module 909, and an image display module 910 as described above and further herein. However, the operations performed by these modules are not limited to those described herein, and the sequence, arrangement, and total number of modules may vary, with the presently described embodiment being solely for example purposes. The software modules may be accessed via a client user interface, for example, a user interface associated with computer 907.

Once the program is launched, a user may select a digital image for analysis. In some embodiments, the user selects an image from a series of images of adjacent serial sections, wherein at least one of the sections has been stained with H&E and other sections have been stained with one or more different IHC stains. In a first step, the user may select an H&E stained slide from the set of serial sections. Through the client interface, a user may invoke annotation module 902, which when executed, for example by the CPU or processor 905, enables a user to identify regions of interest in the H&E stained slide for further analysis, and to identify regions to be excluded from further analysis in the H&E stained slide.

Through the client interface, a user may then invoke the image registration module 904, which when executed for example by the CPU or processor 905, maps the annotations on the H&E stained slide to another slide in the series of images of adjacent serial sections, such as a slide that is marked with an IHC marker.

Through the client interface, a user may also invoke the heat map generation module 906, which when executed, for example by the CPU or processor 905, analyzes the IHC marked slide to assist in identifying potential hot spots. In the illustrated embodiment this is accomplished by applying an image analysis algorithm specific to the tissue and assay to score the whole tumor region, and next by generating a heat map which is a visual display of the image analysis results at low resolution (lower than scanned resolution). For example, with respect to the image analysis step, to analyze a K67, ER or PR slide, an algorithm is used to detect, classify and count the positive and negative nuclei. As another example, for an HER2 slide, a membrane detection algorithm is used. For example, with respect to the low-resolution heat map generation step, a sliding window is used to compute a value related to the scoring metric across the whole slide, with each value corresponding to a pixel in the low-resolution heat map.

The FOV selection module 909 enables a user to select specific regions of the slide (for example hot spot regions) for detailed review. For example, whereas the heat generation map may be a low-resolution version of the slide providing high-level information regarding regions that are densely marked, the FOV view calls up the corresponding high-resolution image and/or image data of the selected region. (See FIG. 11 wherein the FOV is highlighted on the heat map in the thumbnail, and the high resolution image showing detailed scoring metric information computed in the image analysis step of the heat map generation module corresponding to the FOV is shown in the main display.)

The image display module 910 may generate images of the whole slide images (or portions thereof such as when the FOV module is applied), either in their native form (for example so the user may select an image to analyze using the annotation, image registration and/or heat map generation modules) or may generate images that are annotated by the annotation, image registration, heat map generation, and/or FOV selection modules. In addition, the image display module may generate further images of data produced by the image analysis program.

Figure 2:
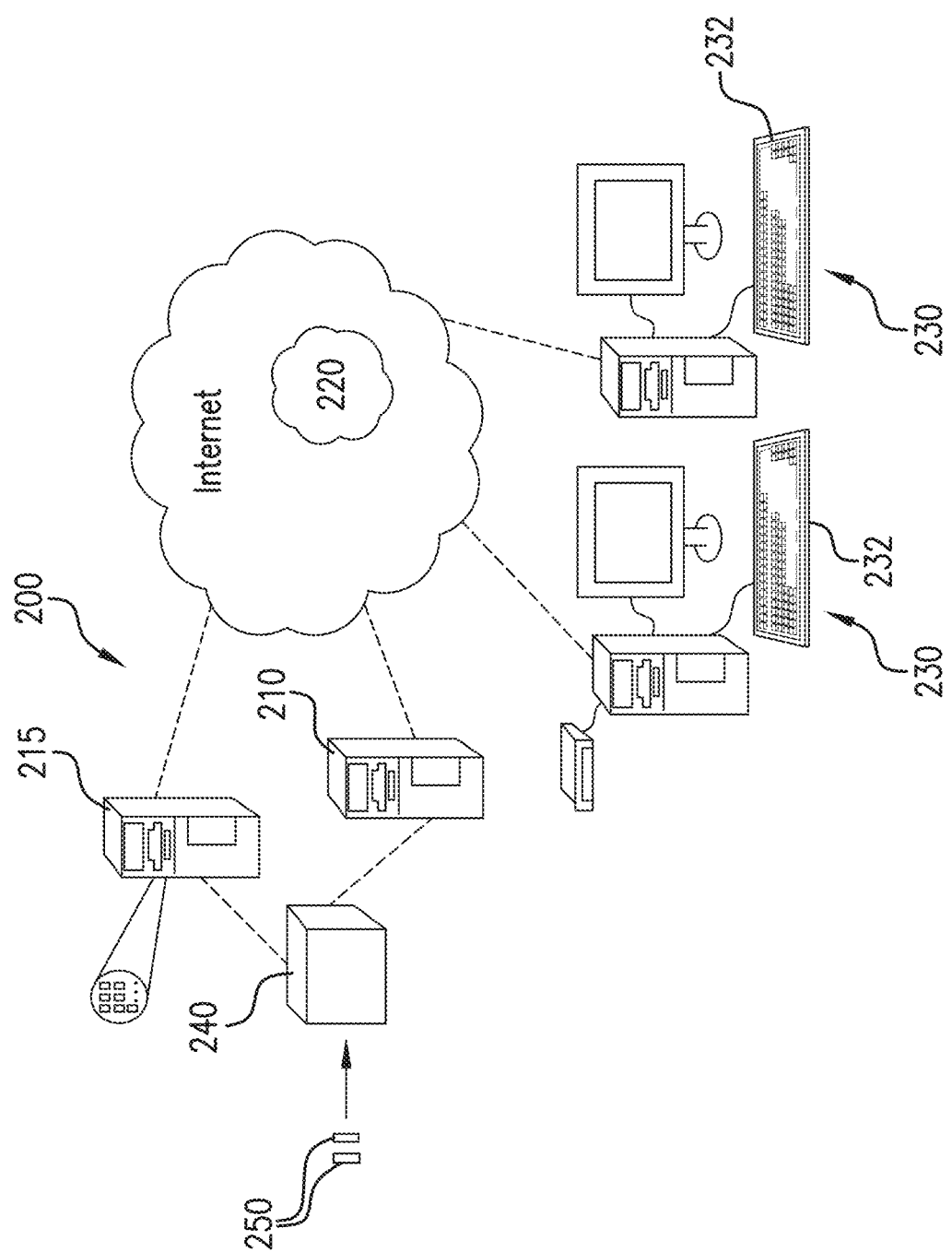
FIG. 2 depicts a network diagram illustrating an embodiment of a networked system in which the devices, systems and methods according to the disclosure may be implemented.

FIG. 2 is a network diagram illustrating an embodiment of a networked system in which the devices, systems and methods according to this disclosure may be implemented. As shown, the system 200 includes a database server 210 and a network-accessible storage device 215, each of which is connected to a network 220. The storage device 215 stores digital images. One or more client computers 230, which may have associated input and output devices such as a keyboard 232, mouse (not shown) and printer (not shown) are also connected to the network 220 by any means known in the art (for example a dedicated connection, a DSL or cable modem, a wireless internet connection, a dial-up modem or the like). The client computer 230 includes a web browser, which is used to access the digital images in the stored device 215. In exemplary embodiments of the present disclosure, cloud storage may be utilized for storing the digital images.

The client computer 230 includes at least one processor configured to execute instructions relating to an image analysis program. The image analysis program, such as described above, may be downloaded to the client computer 230 from the server 210. In some embodiments, the system 200 also includes a scanner 240 for scanning whole slides 250 and producing the digital images, which are then stored in the storage device 215.

As a person of skill understands, implementing the hot spot detection program in the context of a computerized network enables certain activities that may otherwise be limited by stand-alone workstations. For example, pathologists who are not co-located, and indeed may be remote from one another, may collaborate in analyzing images, or the right pathologist may be reached at the right time, independent of location.

FIGS. 1 and 2 illustrate certain elements, which may be present in one or more computer system or network topologies. A person of skill understands that computer systems and networks in which devices and systems according to this disclosure may be implemented may encompass other computer system and network topologies, and may include more or less elements in those other computer system and network topologies. In other words, the embodiments of FIGS. 1 and 2 are not limiting. For example, in some embodiments, cloud storage may be used for storing the digital images.

Accordingly, an exemplary embodiment of a computer system for use in accordance with the present disclosure may include any number of computer platforms or multiple types of computer platforms, such as workstations, personal computers, servers, hand-held devices, multi-processor systems, microprocessor-based or programmable consumer electronics, network PCs, minicomputers, mainframe computers or any other present or future computer.

An exemplary embodiment may also be practiced in distributed computing environments in which tasks are performed by local and/or remote processing devices that are connected (by, for example, hardwired connections, wireless connections, or a combination thereof), in a communications network. In a distributed computing environment, program modules may be located in both local and remote computer storage media including memory storage devices. It will, however, be appreciated by one of ordinary skill in the art that the aforementioned computer platforms as described herein are specifically configured to perform the specialized operations described in the disclosure.

Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Examples of input devices include a keyboard, cursor control devices (e.g., a mouse), a microphone, a scanner, and so forth.

Examples of output devices include a display device (e.g., a monitor or projector), speakers, a printer, a network card, and so forth. Display devices may include display devices that provide visual information, which information typically may be logically and/or physically organized as an array of pixels.

An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device.

In the same or alternative embodiments, applications on a computer may employ an interface that includes what are referred to as "command line interfaces" (often referred to as CLI's). CLI's typically provide a text-based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework. Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related art will appreciate that a processor may be configured in what is generally referred to as 32 or 64 bit architectures, or other architectural configurations now known or that may be developed in the future.

A processor typically executes an operating system, which may be, for example, a Windows-type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer-readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product.

As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote.

In one embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution.

Also, a computer may include one or more library files, experiment data files, and an internet client stored in system memory. For example, experiment data could include data related to one or more experiments or assays.

Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems.

The methods and systems of the present disclosure provide an automated or semi-automated (hereinafter "semiautomated") workflow to assist in selection of sub-regions of digitized tissue images to score. In some embodiments, the methods and systems result in analysis of the whole slide, and identification and ranking of potential hot spots (regions which have a high density of marked objects), facilitating and improving the accuracy of FOV selection. The methods and systems have been found relevant to analyzing biological specimens, and useful in computing tissue analyses scores, for example in immunoscore computations. In some embodiments, the methods and systems of the present disclosure overcome disadvantages known in the prior art, such as FOV selection being un-reproducible and biased in human reader manual FOV selection, as the semi-automatic FOV selection method and system of the present disclosure is able to provide the FOVs via computer without relying on human reader's manual selection.

The computer-implement approach is described herein in further detail for exemplary purposes in connection with the scoring of IHC slides and for use in immunohistochemical computations. The described approach is applicable and can be customized to pick hot spots for slide interpretation and scoring in any single or multiple set of IHC assay stained slides (such as ER, PR, Ki67, HER2, Dual ISH, CD3, CD8, c-MET, PD-L1, etc.) of any biological specimen tissue and of multiple disease types (like breast, prostate, colon, brain, etc. However, although the disclosure is described for exemplary purposes in connection with cancerous tissue and immune markers, wherein each slide is marked with only a single stain, the computer-implemented method is applicable to multi-plexed slides and to any type cell or biological specimen or tumor of any disease or non-disease state, and images that have been subjected to any type of staining. For example the disclosure is applicable to images of biological specimens that have been stained with fluorescent and non-fluorescent stains. And the disclosure is applicable to determinations of type, density and location for any type of cell or group of cells. Also, a person of ordinary skill in the art would recognize that the order of the steps may vary from what is described herein.

Figure 4:
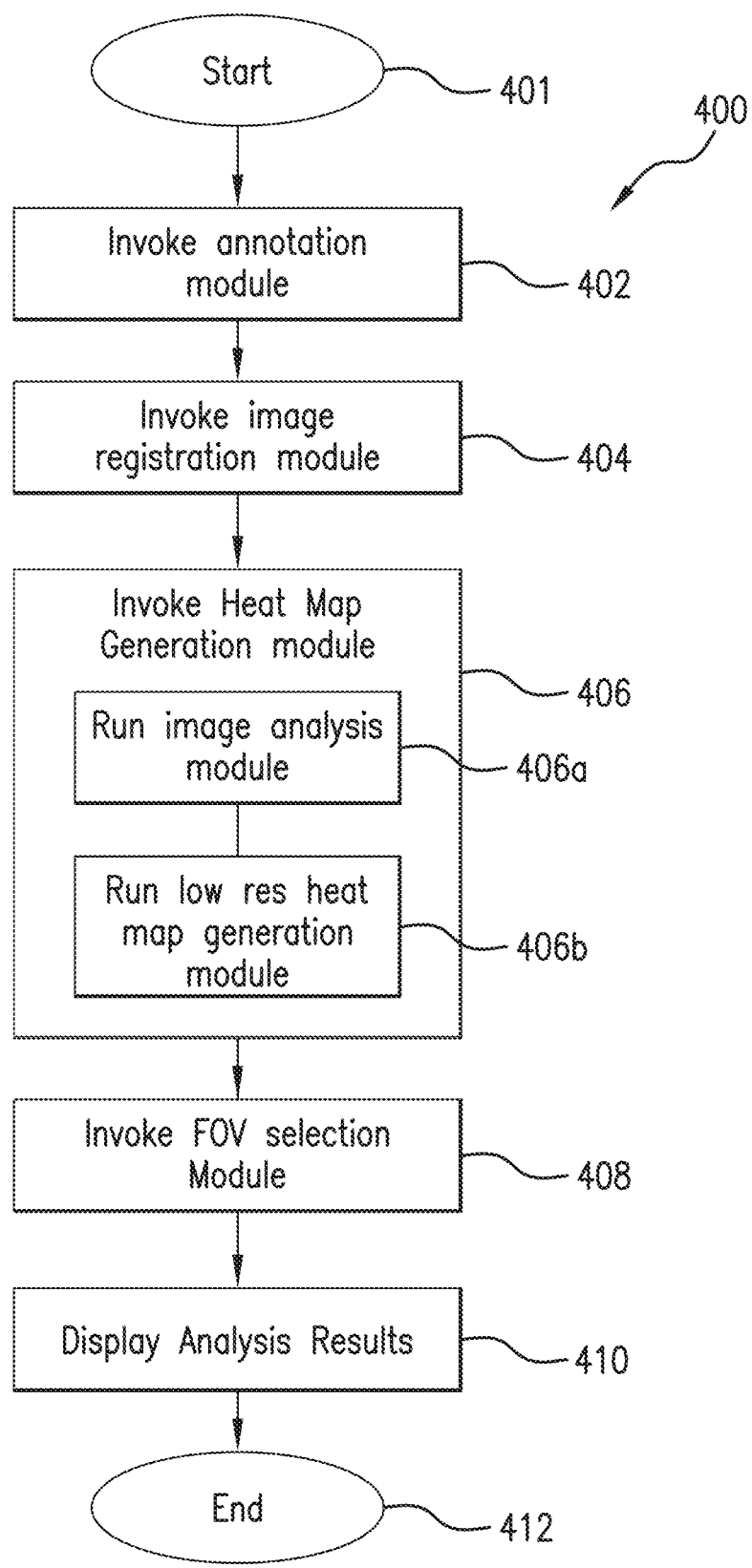
FIG. 4 depicts a workflow diagram for a method of generating a heat map and scoring a slide image in accordance with the present disclosure.

FIG. 4 is a work flow diagram of an embodiment of a protocol according to this disclosure, more specifically a semi-automated workflow and algorithm for selecting FOVs for IHC scoring in accordance with the present disclosure 400. In some embodiments, described in reference to FIG. 4, the method involves annotating a tumor region on a digitized primary staining slide image, registering the annotations from the digitized primary staining slide image to the digitized specific staining slide image, computing a scoring metric of interest (determined by tissue and assay type) across the whole slide for example at the scanned resolution, generating a heat map, for example at low resolution, which provides a high level overview of the scoring metric of interest, selecting one or more fields of view (FOVs) identified by the heat map as possible hot spots, and scoring the specific staining of the one or more FOVs of the digitized staining slide image (for example by using the information calculated in the computation step). In some other embodiments, the method involves annotating a tumor region directly on the digitized specific staining slide image (e.g. the IHC marker slide of interest) and using a similar workflow to thereafter pick hotspots on the specific staining slide image.

In illustrative embodiments, the method starts at block 401 and proceeds to first step 402, which includes invoking the annotation module 902 and selecting a first tumor image from a set of images of adjacent serial sections in a tissue block and annotating the selected tumor image on a digitized primary staining slide image. In some embodiments, the annotations reflect location of tumor regions. In additional embodiments, the image may also be annotated to identify regions to be excluded from analysis (e.g. normal tissue, necrotic regions, etc.). For example, as shown in FIG. 5, this step may include a whole slide scan of an H&E slide and displaying the H&E image in the whole slide viewer application so that a pathologist can annotate tumor regions. In some embodiments, the annotations are done manually. In some embodiments, the annotations may automatically generated by an image analysis algorithm. For example, the tumor annotations on the H&E slide may be generated. (See, e.g., Kien Nguyen et al., "Adaptive whole slide tissue segmentation to handle inter-slide tissue variability", in Medical Imaging 2015: Digital Pathology, Metin N. Gurcan; Anant Madabhushi, Editors, Proceedings of SPIE Vol. 9420 (SPIE, Bellingham, W A 2015), 94200P).

In a second illustrative step 404, the method includes invoking the image registration module 904 and selecting one or more second tumor images from the set of images of adjacent serial sections of the tissue block and registering the annotations from the digitized primary staining slide image to the one or more second images. A purpose of annotation and registration is to limit hot spot selection to tumor regions. For example the one or more second tumor images may be a set of IHC serial section slides to be analyzed such as is shown in FIG. 6, wherein the annotation from the H&E primary stained-slide of step 402 has been transferred to a PR-IHC stained serial secondary slide (6*a*), an ER-IHC stained serial secondary slide (6*b*), a Ki67-IHC stained serial secondary slide (6*c*), and an HER2-IHC stained serial secondary slide.

In some embodiments, image registration may be done manually by visual inspection, wherein the annotated H&E stained slide is visually compared to the IHC image and a user manually annotates corresponding sections on the IHC marked slide. In some embodiments, image registration may be done automatically or semi-automatically using an image registration program such as that described in WO2014/140070, which is hereby incorporated by reference in its entirety.

A heat map is generated in step 406 on the basis of image data associated with the regions defined in the annotation and image registration steps. A heat map is a low-resolution image of the whole slide, where a pixel value in the heat map is correlated to the specific scoring criteria for the slide. The regions in the heat map, which are locally dominant are considered to be hot spots, from which a pathologist selects FOVs to compute the slide level score. Visually, the heat map presents a high-level overview of the scoring metric of interest. For instance, the heat map for a Ki67 slide, which is shown in FIG. 10, is indicative of the percent positivity in the tumor region. "Low resolution" is a relative term, which is intended to mean only that the heat map is displayed at a resolution that is lower than the scanned resolution. In general, the resolution of the heat map is chosen to simplify identification of hot spots while preserving sufficient data for a pathologist to make a meaningful decision regarding hot spots and potential FOVs. In some embodiments, for example a Ki67 whole slide scanned at 20× resolution, the heat map is displayed at 1.25× resolution. A person of skill understands that the specific tissue and analysis factor into the choice of resolution and is capable of selecting a desired or appropriate resolution for display and/or analysis purposes.

In some embodiments, the pixel values in the heat map are generated in a two-step process beginning with step 406a which uses an image analysis algorithm specific to the scoring metric of interest (determined by tissue and assay type, for example the particular IHC algorithm) to analyze and score the whole tumor region at commonly used magnification to compute the score. For example, for breast cancer, IHC markers are scanned and analyzed at 20× resolution, which corresponds to around a pixel size of 0.5 microns on VENTANA COREO whole slide scanner. For example, to analyze a Ki67, ER, PR slide, an algorithm to detect, classify and count the positive and negative nuclei is used. For HER2, a membrane detection algorithm may be used. As the whole tumor region can be quite large the region may be gridded into tiles with each tile being analyzed in parallel either in a multi-threaded environment on a local computer with or without a GPU, or on a distributed computer. A person of skill in the art can select an appropriate tile size for their application with the understanding that the larger the tile, the coarser the resolution and potentially less meaningful information (for example if a tile the size of the tumor region is used, then the heat map will have only one data point). At the same time, a tile that is too small provides less accurate information because the corresponding pixel in the heat map represents the results (for example the average value) for that tile. In general the idea is to balance generating a heat map which is visually easy to analyze but that also has a sufficient level of detail to provide meaningful information and allow meaningful decisions (such as to hot spot regions). In some embodiments, the tile size is chosen to mimic what a pathologist sees under a microscope, for example the tile size may be 1 mm by 1 mm.

In some embodiments, the analysis results from the individual tiles can be saved to a results database on either the local computer or remote server for use in a later step; for example, the same image analysis algorithm used to compute the heat map may also be used to interpret the individual FOVs, with the intent of capturing the same information.

In some embodiments, as shown in step 406b, the second step involves using the analysis results computed in the tumor region to generate a low-resolution heat map. This can be done as illustrated in FIG. 9, by computing the pixel value at a specific location in the heat map from the image analysis results in the corresponding sliding window of desired size and shape on the whole slide. In some embodiments, the sliding window may correspond to a typical-sized image region that a pathologist uses to estimate the average scoring metric values for the region. In this embodiment, a rectangular window of 1 mm×1 mm is used. For example, the detected positive and negative nuclei that are enclosed by the window are clustered into groups, which may correspond to either spatially near single or multiple glandular regions. To group the nuclei into clusters, we used graph partition algorithms. The pixel values in the heat map that correspond to the sliding window are set to the average percent positivity computed for the clusters. For each cluster average percent positivity, which is the proportion of positive tumor in the detected number of nuclei, is computed and set as the pixel values in the heat map. Alternatively, other metrics such as local density of the positive nuclei or average of the average amount of positive staining (computed from DAB channel) can also be used. In the other methods reported in the published literature a local average of the positive staining of the whole slide at a lower magnification is used to compute the heat map (see, e.g., Brey, Eric M; Elie, Nicolas, et al; and, Jesper Molin et al. referenced above). In the approach proposed herein, these methods can be used as an alternative metric or in combination with other methods.

In step 408, the generated heat map is used, either in a semi-automated or automated manner, in the selection of FOV hotspots. As shown in FIG. 10, which is the heat map generated from the Ki67-IHC stained slide of FIG. 6c, a color-coded version of the heat map image, from low to high range, is output to reflect the spatial variation of the metric of interest. Along with the whole slide image of the tissue slide, the heat map is presented to the user in the whole slide image viewer application.

In semi-automated mode, the pathologist can visually review the heat map and click on a particular position on the heat map using the mouse. Once clicked, as shown in FIG. 11, the whole slide viewer display screen is updated to display the scanned high-resolution version of the same region on the whole slide. This enables the user to review and annotate the FOV to score the slides by drawing a region making use of the annotation tools of the whole slide viewer.

In automated mode, an algorithm can be used to rank, select and highlight the hot spots on the heat map image by drawing a visual indicator such as a box on the heat map. The ranking can be done by picking the local maxima within a neighborhood of the values in the heat map and sorting them in order. The user can further investigate the individual regions and pick the appropriate hot spots for scoring.

In step 410, the analysis results, which were computed and stored to memory in step 406a, are retrieved from the results database for the hot spots selected in step 408 and displayed in the whole slide viewer, for example as an analysis results overlay on the annotated regions. From the analysis results computed for the multiple selected FOVs, an aggregate whole slide score can be approximated.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the claims. Accordingly, the foregoing description of various embodiments does not necessarily imply exclusion. For example, "some" embodiments of "other" embodiments may include all or part of "some", "other", "further", and "certain" embodiments within the scope of this disclosure.

The invention claimed is:

1. A method of generating a heat map representation of a specified scoring criteria, the method comprising:
    selecting a digitized staining slide of a tumor image depicting at least part of a tumor;
    computing a scoring criteria specific to the tumor and staining type at scanned resolution; and
    generating a low-resolution heat map by correlating pixel values in the low-resolution heat map to the scoring criteria, wherein correlating the pixel values in the low-resolution heat map to the scoring criteria comprises:
        computing an average value for the scoring criteria in a windowed region of predetermined size in an annotated tumor region which average value correlates to a pixel value; and
        sliding the windowed region across the annotated tumor region to iteratively compute pixel values and generate the low-resolution heat map.

2. The method of claim 1, further comprising:
    annotating the tumor image on the digitized staining slide; and after annotating the tumor image, computing the scoring criteria.

3. The method of claim 2, wherein the digitized staining slide is a digitized primary staining slide and the method further comprises registering annotations from the digitized primary staining slide to a digitized specific staining slide of the tumor image.

4. The method of claim 3, wherein annotating the tumor image comprises displaying the digitized primary staining slide on a display so that a user can manually demarcate a whole tumor region using an input device.

5. The method of claim 3, wherein annotating the tumor image in the digitized primary staining slide comprises processing the digitized primary staining slide with a tumor identification algorithm so that the tumor image is automatically demarcated.

6. The method of claim 3, wherein, registering annotations from the digitized primary staining slide includes applying an inter-marker image registration algorithm to map tumor region annotations from the digitized primary staining slide to the digitized specific staining slide.

7. The method of claim 1, further comprising saving the computed scoring criteria to a database, and selecting Field-of-Views from locally dominant regions in the low-resolution heat map which returns the computed scoring criteria for the selected Field-of-Views to obtain a slide-level score.

8. The method of claim 1, wherein computing scoring criteria comprises gridding the annotated tumor region into tiles of a predetermined size and computing the scoring criteria for each tile at scanned resolution.

9. The method of claim 1, further comprising using an algorithm to rank, select and highlight hot spot regions having a high density of specific staining.

10. The method of claim 9, wherein ranking comprises selecting local maxima within a predetermined neighborhood of values in the low-resolution heat map and sorting them in order.

11. The method of claim 1, wherein computing scoring criteria comprises computing multiple scoring criteria and generating a heat map comprises generating a heat map for each one of the multiple scoring criteria.

12. A system comprising:
    one or more data processors; and
    a non-transitory computer readable storage medium containing instructions which, when executed on the one or more data processors, cause the one or more data processors to perform actions including:
        selecting a digitized staining slide of a tumor image depicting at least part of a tumor;
        computing a scoring criteria specific to the tumor and staining type at scanned resolution; and
        generating a low-resolution heat map by correlating pixel values in the low-resolution heat map to the scoring criteria, wherein correlating the pixel values in the low-resolution heat map to the scoring criteria comprises:
            computing an average value for the scoring criteria in a windowed region of predetermined size in an annotated tumor region which average value correlates to a pixel value; and
            sliding the windowed region across the annotated tumor region to iteratively compute pixel values and generate the low-resolution heat map.

13. The system of claim 12, wherein the actions further include annotating the tumor image on the digitized staining slide; and after annotating the tumor image, computing the scoring criteria.

14. The system of claim 13, wherein the digitized staining slide is a digitized primary staining slide and the method further comprises registering annotations from the digitized primary staining slide to a digitized specific staining slide of the tumor image.

15. The system of claim 14, wherein annotating the tumor image comprises displaying the digitized primary staining slide on a display so that a user can manually demarcate a whole tumor region using an input device.

16. A computer-program product tangibly embodied in a non-transitory machine-readable storage medium, including instructions configured to cause one or more data processors to perform actions including:
    selecting a digitized staining slide of a tumor image depicting at least part of a tumor;
    computing a scoring criteria specific to the tumor and staining type at scanned resolution; and
    generating a low-resolution heat map by correlating pixel values in the low-resolution heat map to the scoring criteria, wherein correlating the pixel values in the low-resolution heat map to the scoring criteria comprises:
        computing an average value for the scoring criteria in a windowed region of predetermined size in an annotated tumor region which average value correlates to a pixel value; and
        sliding the windowed region across the annotated tumor region to iteratively compute pixel values and generate the low-resolution heat map.

17. The computer-program product of claim 16, wherein the actions further include:
    saving the computed scoring criteria to a database, and selecting Field-of-Views from locally dominant regions in the low-resolution heat map which returns the computed scoring criteria for the selected Field-of-Views to obtain a slide-level score.

18. The computer-program product of claim 16, wherein computing scoring criteria comprises gridding the annotated tumor region into tiles of a predetermined size and computing the scoring criteria for each tile at scanned resolution.

* * * * *